United States Patent
Butler et al.

(10) Patent No.: US 8,246,665 B2
(45) Date of Patent: Aug. 21, 2012

(54) POSTERIOR CERVICAL CROSS CONNECTOR ASSEMBLIES

(75) Inventors: Michael S. Butler, St. Charles, IL (US); Daniel Predick, Chicago, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 429 days.

(21) Appl. No.: 12/645,110

(22) Filed: Dec. 22, 2009

(65) Prior Publication Data

US 2010/0160981 A1 Jun. 24, 2010

Related U.S. Application Data

(60) Provisional application No. 61/139,737, filed on Dec. 22, 2008.

(51) Int. Cl.
*A61B 17/70* (2006.01)
*A61B 17/04* (2006.01)
*A61B 17/86* (2006.01)
*A61F 2/08* (2006.01)

(52) U.S. Cl. ........................................ 606/308; 606/251

(58) Field of Classification Search ................... 606/250, 606/25, 264, 265, 275, 278, 305–308
See application file for complete search history.

(56) References Cited

U.S. PATENT DOCUMENTS

| | | | |
|---|---|---|---|
| 5,142,953 A | 9/1992 | Lin | |
| 5,217,497 A | 6/1993 | Mehdian | |
| 5,688,272 A * | 11/1997 | Montague et al. | 606/252 |
| 5,885,286 A * | 3/1999 | Sherman et al. | 606/270 |
| 5,968,008 A | 10/1999 | Grams | |
| 6,730,089 B2 * | 5/2004 | Jackson | 606/270 |
| 7,204,838 B2 * | 4/2007 | Jackson | 606/270 |
| 7,250,052 B2 | 7/2007 | Landry et al. | |
| 7,837,714 B2 * | 11/2010 | Drewry et al. | 606/250 |
| 8,100,909 B2 * | 1/2012 | Butler et al. | 606/60 |
| 2005/0137602 A1 | 6/2005 | Assell et al. | |
| 2009/0254125 A1* | 10/2009 | Predick | 606/264 |
| 2010/0036420 A1* | 2/2010 | Kalfas et al. | 606/250 |
| 2010/0094345 A1* | 4/2010 | Saidha et al. | 606/250 |

* cited by examiner

*Primary Examiner* — Kevin T. Truong
*Assistant Examiner* — David Bates
(74) *Attorney, Agent, or Firm* — Foley & Lardner LLP

(57) ABSTRACT

A spinal cross connector head assembly and a cross connector assembly utilizing the spinal cross connector head assembly are configured for fixation to an existing spinal rod bone screw head. The spinal cross connector head assembly has one or more components which incorporate one or more breakaway portions that aid in the installation of the cross connector head assembly onto a polyaxial spinal rod bone screw assembly. The spinal cross connector assembly includes first and second spinal cross connector head assemblies each of which is configured for fixation to existing, adjacent spinal rod screw heads and connection with a cross connector rod. Each spinal cross connector rod head assembly has a dual breakaway system including a cross connector head component having a breakaway collar that, once detached, provides a polyaxial cross connector head, and a set screw component having a breakaway set screw that, once detached, provides fixation of the orientation of the polyaxial cross connector head relative to the polyaxial spinal rod bone screw head.

14 Claims, 16 Drawing Sheets

POSTERIOR CERVICAL CROSS CONNECTOR ASSEMBLIES

RELATED APPLICATIONS

This patent application claims the benefit of and/or priority to U.S. Provisional Patent Application Ser. No. 61/139,737 filed Dec. 22, 2008, entitled "Posterior Cervical Cross Connector Assembly" the entire contents of which is specifically incorporated herein by this reference.

BACKGROUND OF THE INVENTION

1. Field of the Invention

The present invention relates to relates to spinal fixation devices that are attached onto a patient's spine such as spinal rods and spinal rod screws (spinal rod assemblies) and, more particularly, to spinal cross connectors for attachment to adjacent spinal rod assemblies.

2. Background Information

There are many medical situations such as disease, injury, trauma or deformity, where it is necessary to align, hold, maintain and/or fix a desired relationship between adjacent vertebrae of the spine. In order to accomplish this goal, orthopedic spinal surgeons utilize spine fixation devices that are attachable to the posterior of various adjacent vertebrae of the affected area of the spine. These spine fixation devices provide the desired relationship between adjacent vertebrae. Spine fixation devices typically include a spinal fixation element, such as a relatively rigid fixation rod (e.g. a spine or spinal rod) that is connected to adjacent vertebrae through attachment of the rod to anchor devices (e.g. bone screw/rod head assemblies) implanted into the vertebrae. As such, spine fixation devices may be termed spine fixation assemblies.

Typically, spine fixation rods are placed on opposite sides of the spinous process in a substantially parallel relationship. The spine fixation rods may have pre-determined contours according to properties of the target implantation site and/or with regard to a desired spatial, vertebral relationship. The bone screw/rod head assemblies are typically implanted into the pedicle or pedicle area of the vertebra. Once installed, the spine fixation assemblies hold the vertebrae in a secure spatial relationship.

It may also be necessary in some circumstances, however, such as in cervical spine fixation applications, to provide a cross connector at one or more points between the two spine fixation assemblies in order to provide additional stability to the structure. Particularly, adjacent spinal fixation rod assemblies can be made more robust by using a cross connector to bridge the pair of spinal rod assemblies.

While current spinal cross connectors are effective, problems exist such as in mounting and maintaining the cross connector in a desired position and orientation with respect to the spinal rods. Other problems also exist with current cross connectors such as height limitations, sizing, locking and ease of installation issues.

Accordingly, there presently exists a need for an improved spinal cross connector that can be easily installed and securely attached to and between spinal rod fixation assemblies. There also presently exists a need for an improved spinal cross connector head assembly that can be easily installed onto a spinal rod bone screw head of a spinal rod bone screw head assembly.

SUMMARY OF THE INVENTION

A spinal cross connector head assembly for a spinal cross connector is configured for fixation to an existing spinal rod bone screw head. The spinal cross connector head assembly has one or more components which incorporate one or more breakaway portions that aid in the installation of the cross connector head assembly onto a polyaxial spinal rod bone screw assembly.

In one form, the present invention is a spinal cross connector head assembly configured for fixation to a spinal rod bone screw head of a polyaxial spinal rod bone screw assembly. The spinal cross connector head assembly has a breakaway collar that, once detached, provides a polyaxial cross connector head. The polyaxial cross connector head allows for multi-planar cross connector rod placement. Fixation of the orientation of the polyaxial cross connector head is achieved through placement of a set screw in the polyaxial cross connector head.

In one form, the present invention is a spinal cross connector assembly for fixation between existing, adjacent spinal rod assemblies. The spinal cross connector assembly includes first and second spinal cross connector head assemblies each of which is configured for fixation to existing, adjacent spinal rod screw heads and connection with a cross connector rod. Each spinal cross connector rod head assembly has a breakaway collar that, once detached, provides a polyaxial cross connector head. The polyaxial cross connector heads thereby allow for multi-planar placement of the cross connector rod. Fixation of the orientation of the polyaxial cross connector heads is achieved through placement of a set screw in the polyaxial cross connector head.

In one form, the cross connector is a spinal cross connector head assembly configured for fixation to a spinal rod bone screw head of a polyaxial spinal rod bone screw assembly. The spinal cross connector head assembly has a dual breakaway system including a cross connector head component having a breakaway collar that, once detached, provides a polyaxial cross connector head, and a set screw component having a breakaway set screw that, once detached, provides fixation of the orientation of the polyaxial cross connector head relative to the polyaxial spinal rod bone screw head.

In one form, the present invention is a spinal cross connector assembly for fixation between existing, adjacent spinal rod assemblies. The spinal cross connector assembly includes first and second spinal cross connector head assemblies each of which is configured for fixation to existing, adjacent spinal rod screw heads and connection with a cross connector rod. Each spinal cross connector rod head assembly has a dual breakaway system including a cross connector head component having a breakaway collar that, once detached, provides a polyaxial cross connector head, and a set screw component having a breakaway set screw that, once detached, provides fixation of the orientation of the polyaxial cross connector head relative to the polyaxial spinal rod bone screw head.

In a particular form, the spinal cross connector head or spinal cross connector rod head assembly is characterized by a cross connector head body defining a screw head and the breakaway collar. A depressor tab is situated within the rod head body which serves, in part, to retain the collar in a poly-axially movable relationship with the screw head once the collar is broken away from the screw head. The screw head is threadedly received in the existing spinal rod screw head. Application of approximately 30 in-lbs detaches the collar from the screw head once the screw head is situated in the existing spinal rod screw head. A set screw is received in the collar once the cross connector rod is situated therein and oriented along with the screw head. The set screw retains the cross connector rod in the screw head while simultaneously retaining the existing spinal rod within the existing screw head. The set screw may include a breakaway top that is detached and removed once the orientation of the collar is set.

A spinal cross connector assembly fashioned in accordance with the present principles as embodied in the present spinal components, allows for placement thereof where there is limited or no availability on a 3.5 mm spinal rod. Construct height is increased from approximately 10 mm to only 15 mm. The present spinal cross connector replaces standard breakaway systems. While the present spinal cross connector is preferably used in cervical spine applications, it can be used in other spine locations if desired.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 1 is a perspective view of a spine fixation construct consisting of adjacent, single level spinal rod assemblies such as are affixed onto the spine of a patient having a cross connector assembly fashioned in accordance with the present principles mounted thereto and between;

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non discussed features may be inherent in component geometry and/or configuration.

DETAILED DESCRIPTION OF EMBODIMENTS OF THE INVENTION

Figure 1:
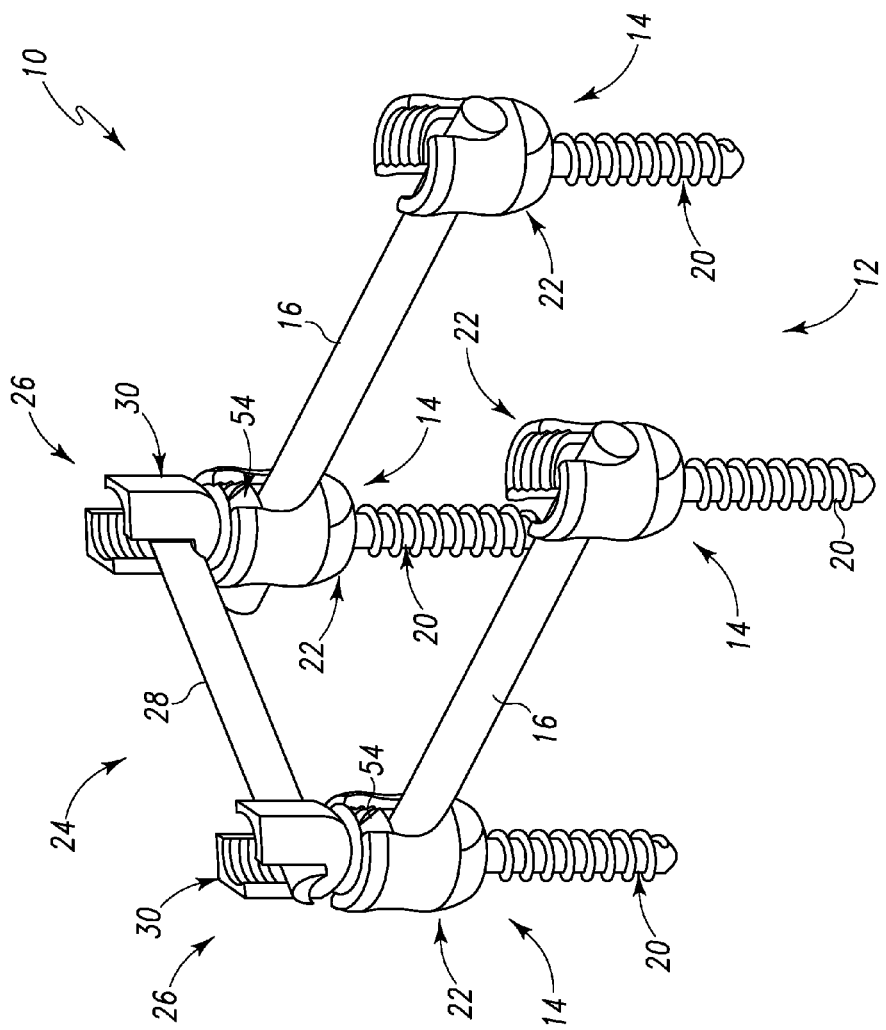

Referring to FIG. 1, there is depicted a perspective view of a spine fixation construct, generally designated 10, of which would be used in spine stabilization situations. The spine fixation construct 10 shown in FIG. 1 comprises an existing spine stabilization system, generally designated 12, and a cross connector assembly 24 and its accompanying components as described herein, according to the present principles, affixed to the existing spine stabilization system 12. The cross connector assembly 24 and is accompanying components are made from a biocompatible material such as titanium or stainless steel. However, other biocompatible material, materials and/or compounds may be employed.

The existing spine stabilization system 12 is shown as a single level construct that is configured to attach to and span two adjacent vertebrae (not shown) and consists of two, adjacent spine rod assemblies. Each spine rod assembly has two bone screw assemblies 14 and a spine rod 16. Each bone screw assembly 14 includes a bone screw 20 and a screw head 22. The bone screw 20 includes a threaded shaft 36 with a rounded head 38 (see, e.g. FIGS. 2 and 3). The threaded shaft 36 is adapted to be received in a vertebra while the rounded head 38 is adapted to be received by the screw head 22. The screw head 22 is adapted to receive and retain the spine rod 16. Not shown on the two front screw heads 22 is a set screw for locking the spine rod 16 into the screw head 22. It should be appreciated that while two spine rod assemblies are shown as being identical, they need not be. Moreover, while not shown, the present cross connector assembly 24 may be used with multi-level spine rod assemblies.

Figure 9:
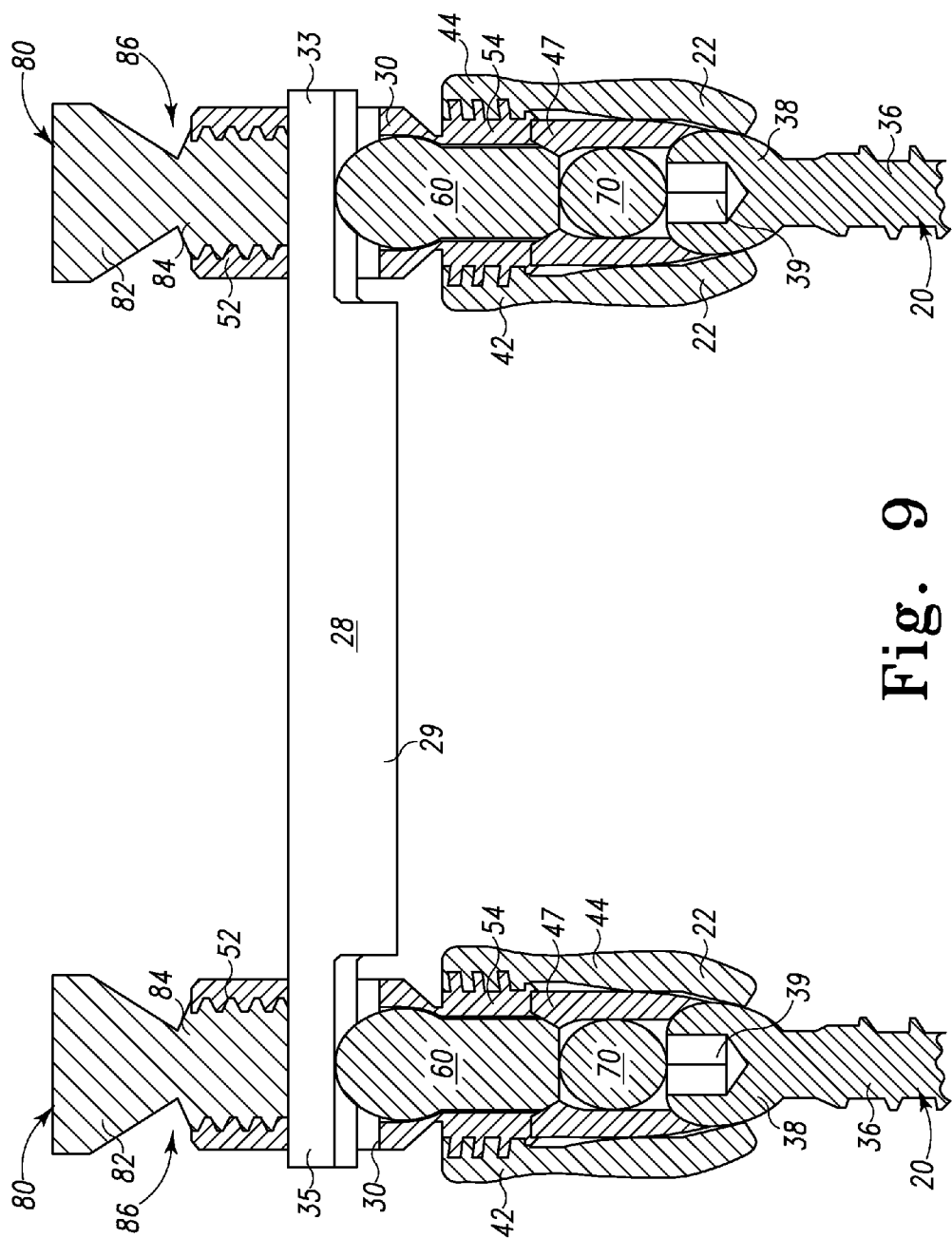
FIG. 9 is a side sectional view of the cross connector assembly disposed on and between polyaxial spinal rod screw assemblies of adjacent spinal rod fixation assemblies with a set screw disposed in each cross connector head.
Figure 10:
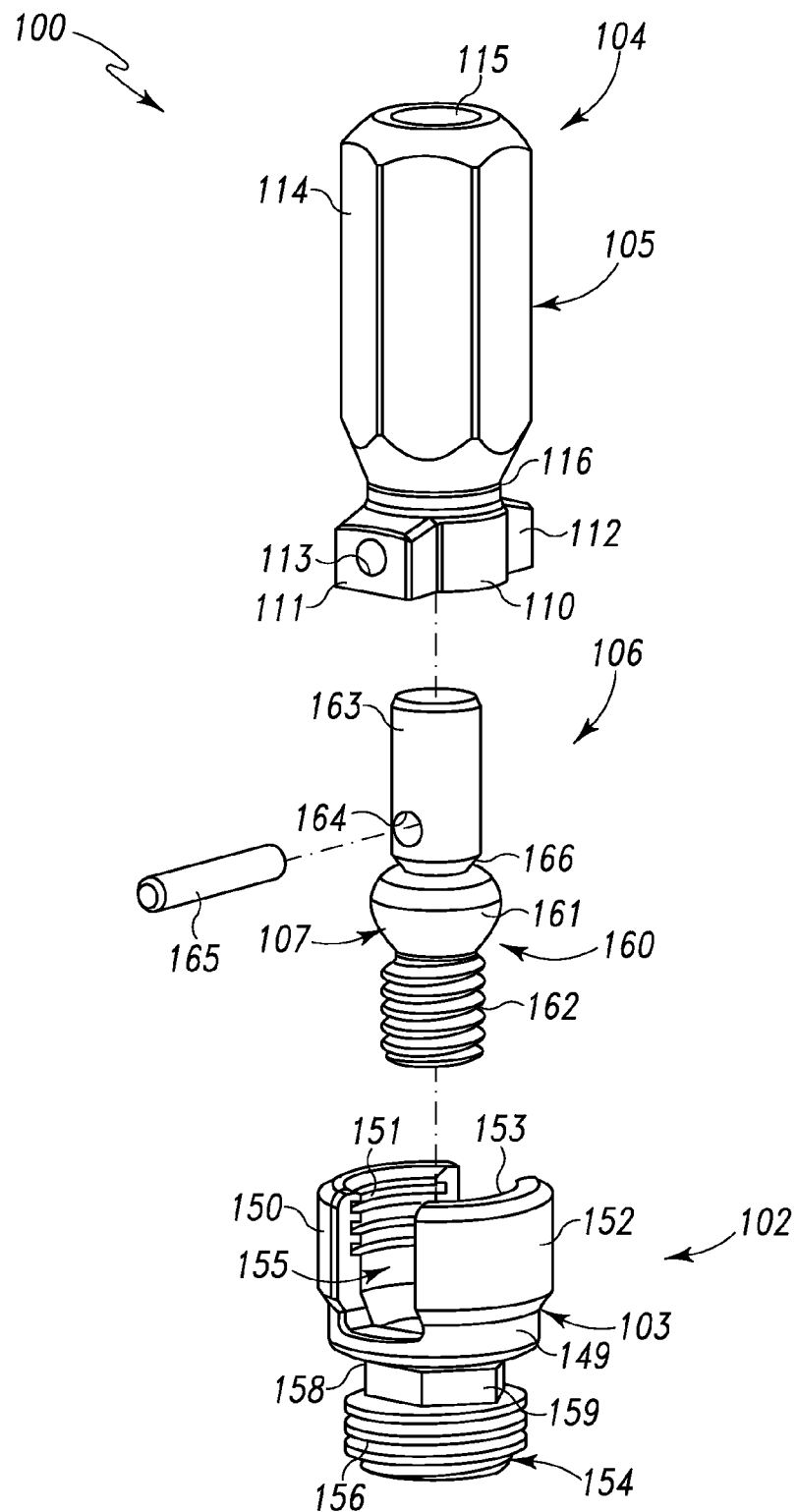
FIG. 10 is an exploded perspective view of another embodiment of a cross connector head assembly for a cross connector assembly, the cross connector head assembly shown before installation on a polyaxial spinal rod bone screw assembly.

The present cross connector assembly 24 comprises two cross connector rod or cross connector heads 26 according to the present principles, and a cross connector rod 28, the configuration of which can best be seen in cross section in FIG. 9. The cross connector rod 28 is adapted to be received in and span between the two cross connector heads 26. A cross connector head 26 is characterized by a body defining an upper portion or rod head portion 30 and a lower portion or set screw portion 54. The lower or set screw portion 54 is configured to be threadedly received in the existing screw head 22. The upper or rod head portion 30 is configured to receive the cross connector rod 28 and a final set screw 80 (see FIG. 9).

Figure 4:
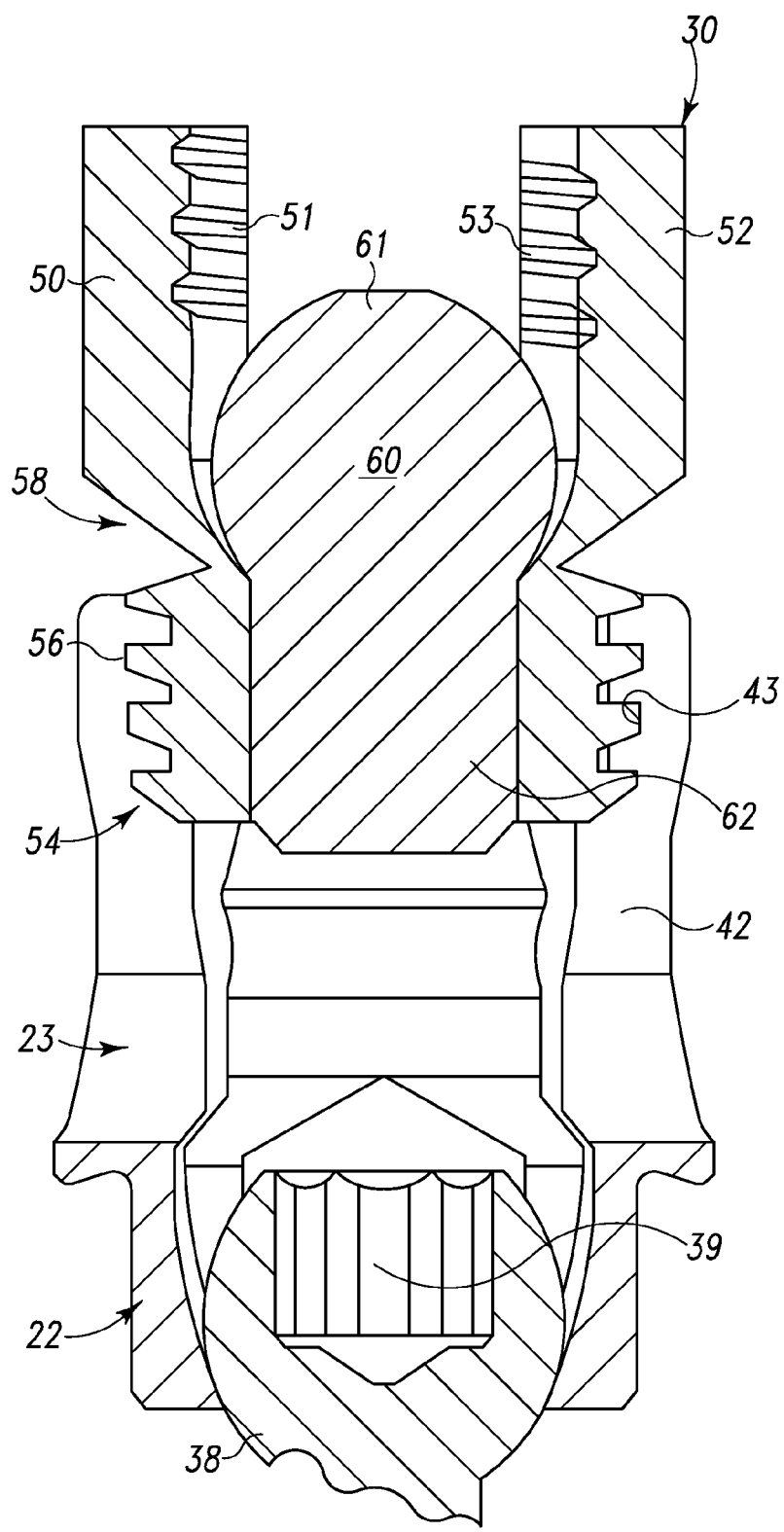
FIG. 4 is an enlarged portion of the sectional view of the polyaxial spinal rod bone screw assembly and cross connector head assembly of FIG. 3 taken along circle 4-4 of FIG. 3.
Figure 5:
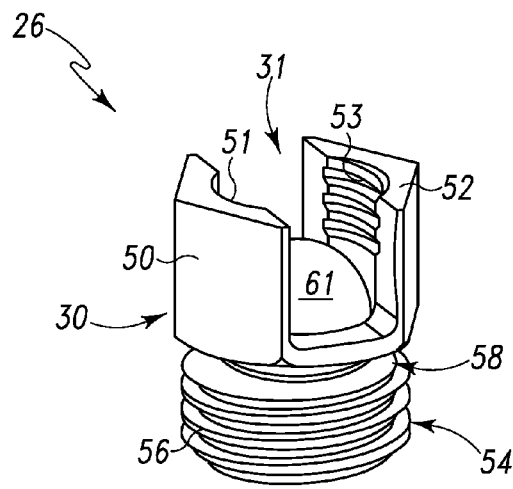
FIG. 5 is an enlarged perspective view of the cross connector head assembly of the cross connector assembly situated on a depressor tab thereof.
Figure 6:
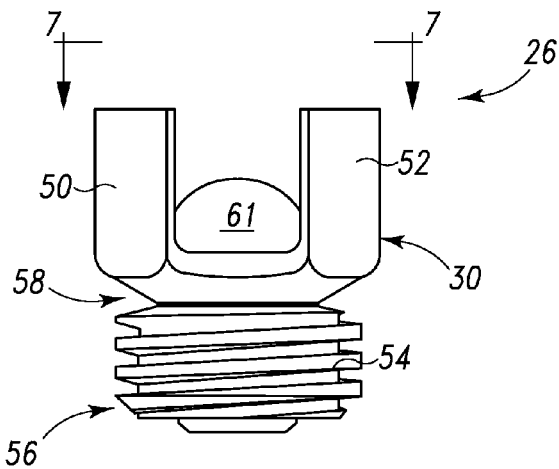
FIG. 6 is a side view of the cross connector head assembly and depressor tab of FIG. 5.
Figure 7:
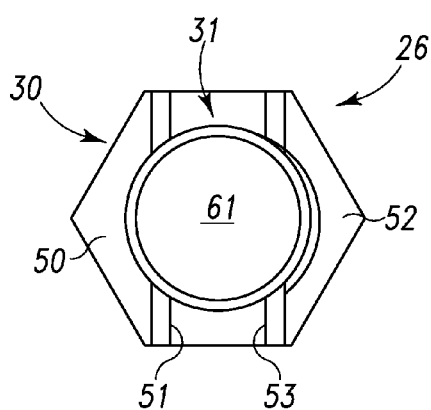
FIG. 7 is a top view of the cross connector head assembly and depressor tab of FIG. 5 taken along line 7-7 of FIG. 6.

Referring to FIGS. 5-7, various views of the cross connector head 26 are shown. The lower or set screw portion 54 of the cross connector head 26 is generally cylindrical and includes external threads 56. In particular, these threads 56 are configured to be received by inner threads 43 of the first side 42 of the screw head 22 and inner threads 45 of the second side 44 of the screw head 22 (see, e.g. FIGS. 3, 4 and 8) in order to connect the cross connector head 26 to the existing screw head 22. The upper cross connector head portion 30 of the cross connector head 26 is connected to the lower portion 54 at or by a breakaway junction or juncture 58. The upper cross connector head portion 30 is generally U-shaped and thus defines first and second sides 50, 52. The first and second sides 50, 52 define a slot 31 for receipt of the cross connector rod 28 and particularly, of a flat portion (e.g. 33 or 35) of the cross connector rod 28 (see, e.g. FIG. 9). Additionally, the first side 50 has a threaded inner surface 51, while the second side 52 has a threaded inner surface 52. The threads 51, 53 are configured to receive threads of a set screw 80 (see FIG. 9). The cross connector head 26 of FIGS. 5-7 is shown in relationship to the upper or ball portion 61 of a peg 60 of the rod head assembly (see, e.g. FIGS. 3, 4, 8 and 9).

For use, the upper portion 30 of the cross connector head 26 is broken or detached from the lower portion 54 at the junction 58. Once detached, since the upper portion 30 is retained by the head 61 of the peg 60 and the lower portion 54 is retained relative to the head 61, the upper portion 30 is rotationally, multi-axially or poly-axially free to rotate about the lower portion 54 and thus the existing bone screw assemblies 14 until fixed by the set screw 80. This allows for various orientations of the rod head, the cross connector rod and the cross connector in general.

Figure 2:
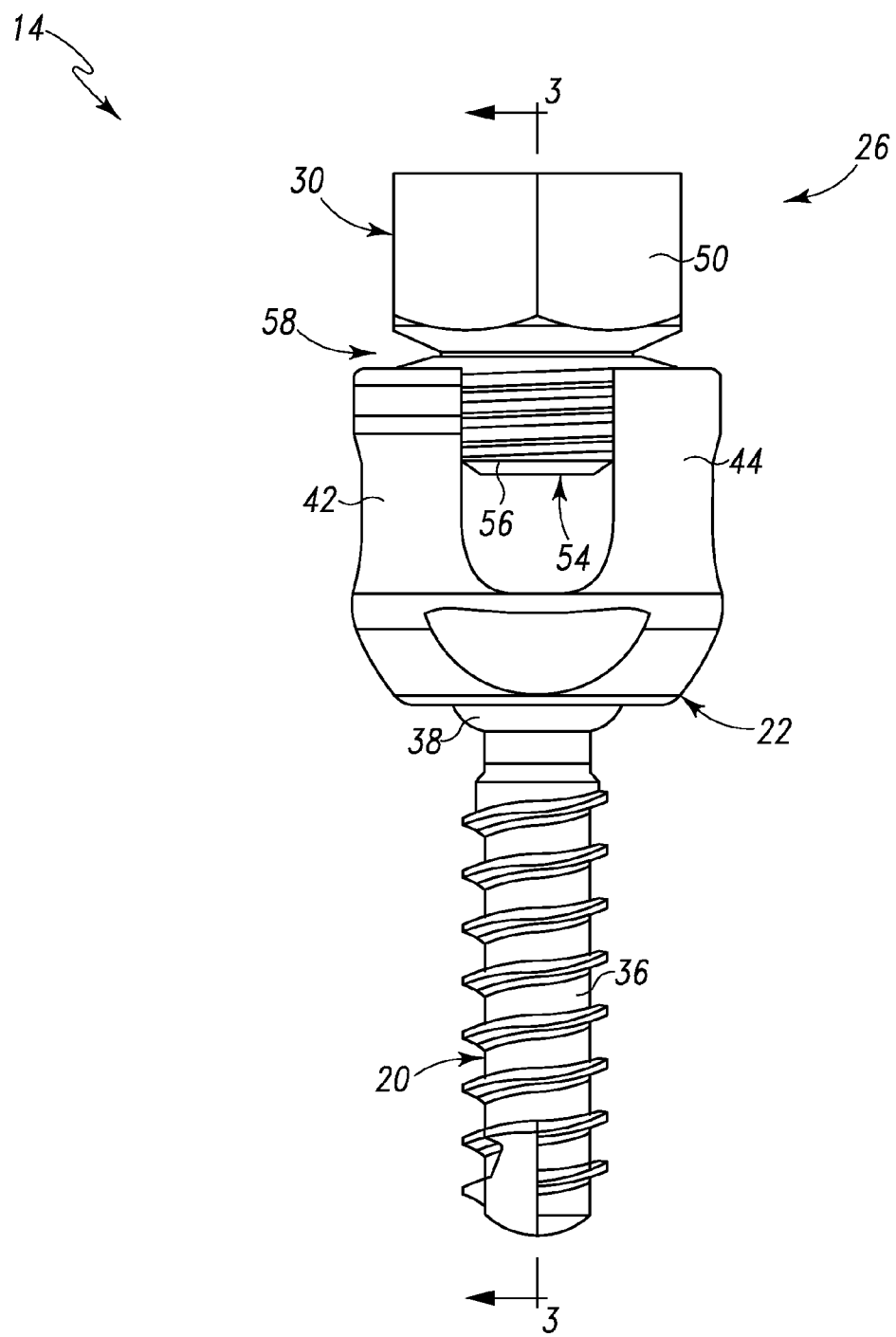
FIG. 2 is an enlarged side view of a polyaxial spinal rod bone screw assembly of the spinal rod assemblies of FIG. 1 having a cross connector head assembly of the cross connector assembly threaded thereon.
Figure 3:
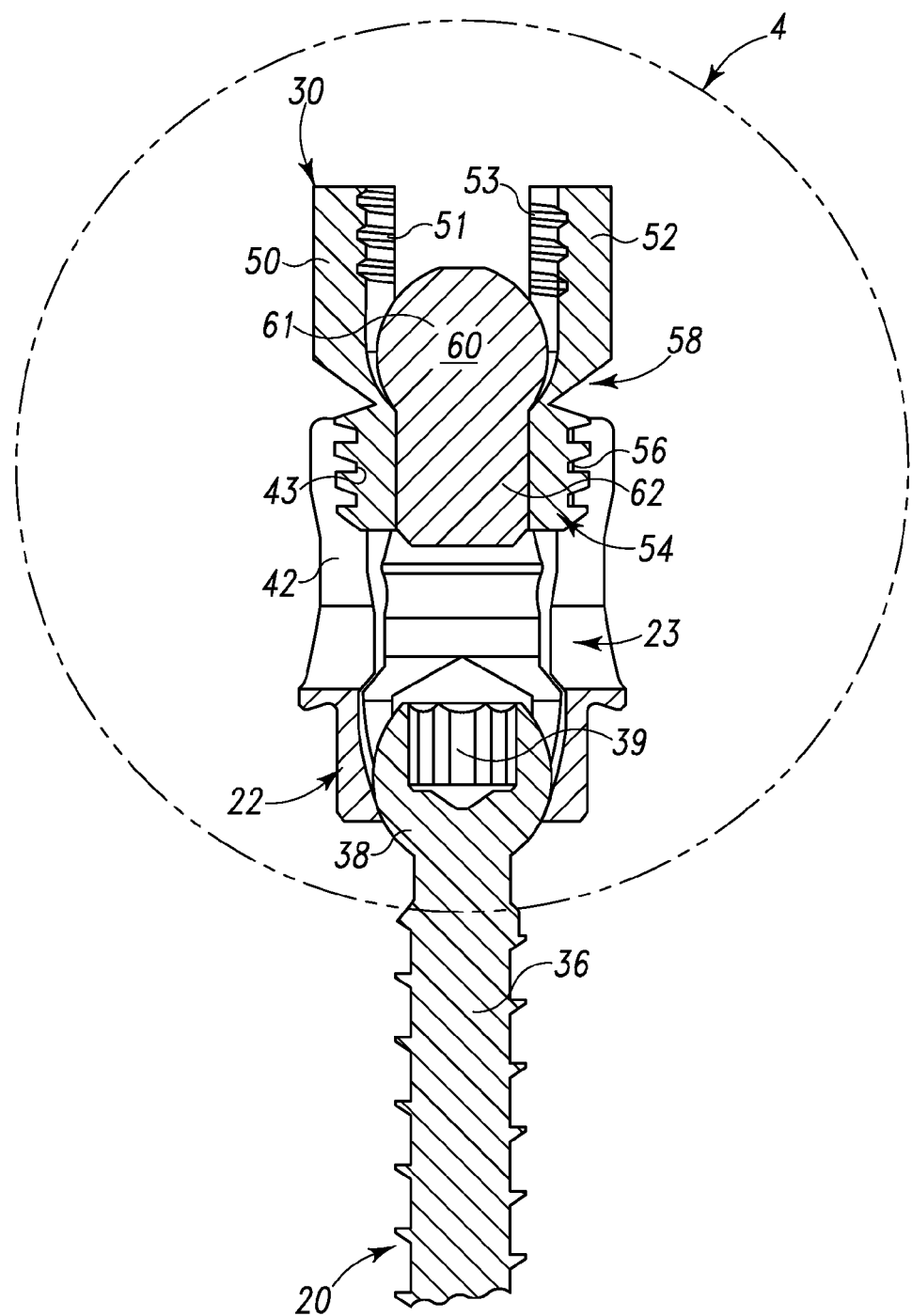
FIG. 3 is a sectional view of the polyaxial spinal rod bone screw assembly and cross connector head assembly taken along line 3-3 of FIG. 2.

FIG. 2 shows an enlarged side view of one of the screw assemblies 14 with the present cross connector rod head 26 situated thereon. The spine rod 16 is not shown therein for simplicity. The spine rod 16 would, however, extend through spine rod cavity 23 in the head 22 (see FIG. 3). The cross connector head 26 is threadedly received by the screw head 22. FIGS. 3 and 4 illustrate the various components thereof and their positioning in a cross-sectional view taken along line 3-3 of FIG. 2 and an enlargement of FIG. 3.

The generally U-shaped bone screw head 22, consisting of first and second side walls 42 and 44, threadedly receives the cross connector head 26. Particularly, the first side wall 42 has inner threads 43 while the second side wall 44 has inner threads 45. The threads 56 of the screw portion 54 of the screw head 22 are received by the threads 43, 45. The peg 60, situated within the cross connector head 26, provides the platform for poly-axial movement of the upper portion 30 relative to the lower portion 54 of the cross connector head 26 while also providing fixing of the existing spine rod 70 and of the orientation of the existing bone screw head 22 relative to the existing bone screw 20.

Figure 8:
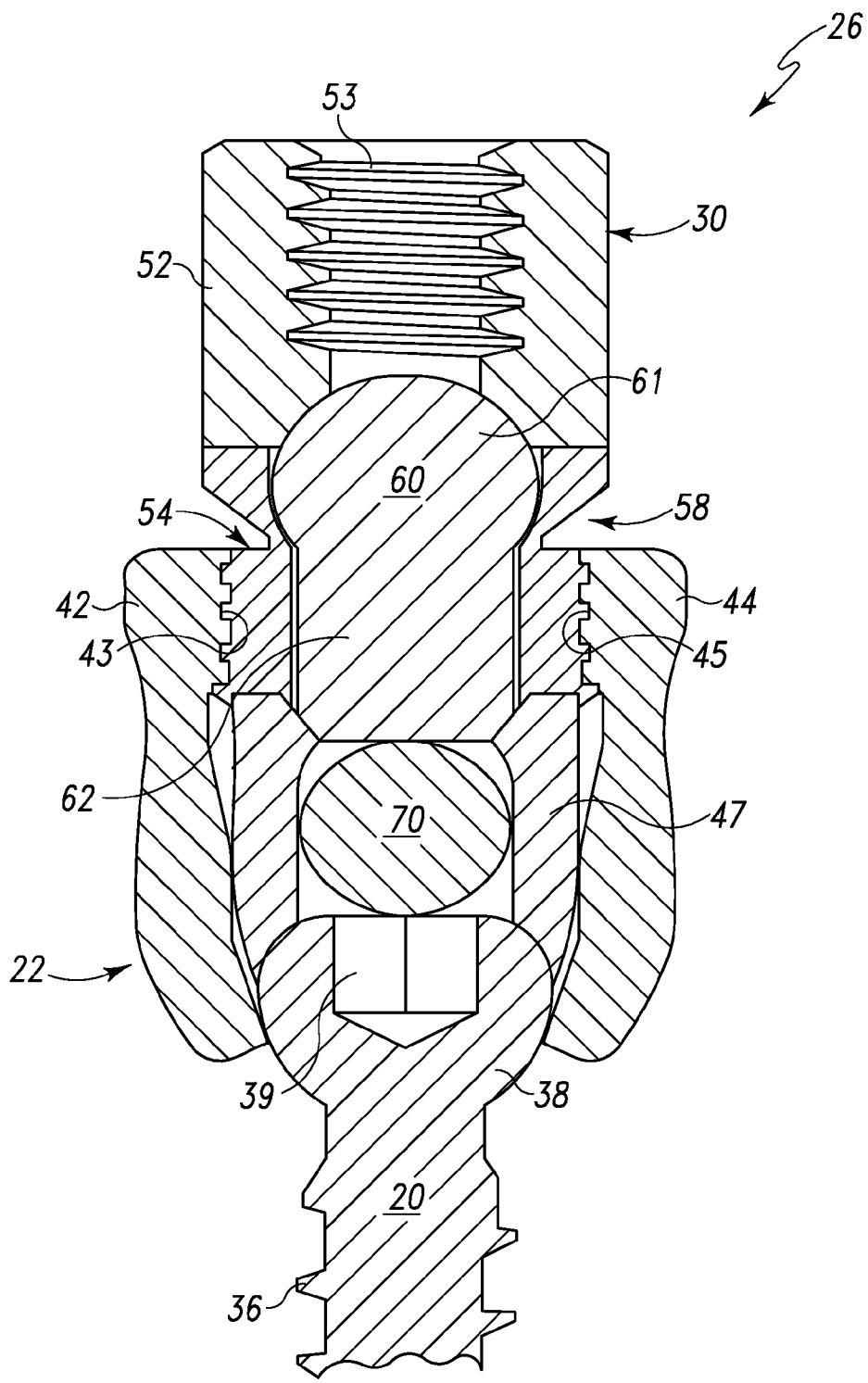
FIG. 8 is an enlarged side sectional view of the cross connector head assembly of the cross connector assembly situated on the polyaxial spinal rod bone screw assembly of the existing spinal rod fixation assembly of FIG. 1.

In FIG. 8, it can be seen that the present cross connector rod head 26 and peg 60 (i.e. a cross connector rod head assembly) serves not only to provide a fixation point for the cross connector rod 28, but to provide fixation of the existing spine rod 70 within the existing bone screw assembly 14 and of the orientation of the bone screw head 22 relative to the bone screw 20. Depression of the peg 60 against the existing spine rod 70 fixes the spine rod 70 within the sleeve 47 of the bone screw head 22. Depression of the sleeve 47 against the head 38 of the bone screw 20 expands the bottom of the sleeve 47 to wedge itself between the inside of the bone screw head 22 and the head 38 of the bone screw 20. This provides the fixation for the bone screw head orientation relative to the bone screw.

Referring to FIG. 9, there is depicted a cross-sectional view of the present cross connector assembly 24 of FIG. 1 wherein a final set screw 80 has been installed on the two rod heads 30 thereof in order to set the orientation of the cross connector. The set screw 80 defines an upper portion or head 82 that is generally conical in shape and a lower portion or screw 84 joined at a breakaway junction 86. The head 82 allows placement of the set screw 80 and particularly the screw 84 in the threads 51 and 53 of the sides 50 and 52 of the rod head portion 30 (see, e.g., FIGS. 3, 4 and 8). The screw 84 is threaded into the rod head portion 30 to contact the cross connector rod 28 and, particularly, the end or flat section (33 or 35) of the cross connector rod 28. The end or flat section 33/35 of the cross connector rod 28 presses against the peg 60 that, in turn, presses against the spine rod 70 and sleeve 47 of the screw head assembly 22 to retain the spine rod 70 relative to the screw head 22 and the orientation of the screw 20 relative to the screw head assembly 22.

Thereafter, the head 82 of the set screw 80 may be detached or broken from the screw 84 at the junction 86. The head 82 would preferably be removed at no more than 30 in-lbs, but may be adjusted as desired. It should be appreciated that while the rod head portions 30 are shown oriented in an upright position relative to the screw 54, they can be oriented in any poly-axial position relative to the screw 54. The cross connector rod 28 may thus be oriented accordingly between the two rod head portions 30.

Referring now to FIGS. 10-18 and particularly 10-12, there is depicted another embodiment of a cross connector head assembly (or cross connector rod head assembly) generally designated 100 that is configured to be received onto a spinal rod bone screw head (e.g., see spinal rod bone screw head 230 of FIG. 13) of a spinal rod bone screw assembly (e.g. see spinal rod bone screw assembly 201 of FIG. 13) as is the cross connector head assembly of FIGS. 1-9. The cross connector head assembly 100 provides single tool installation thereof—i.e. set screw lockup of the orientation of the host spinal rod bone screw assembly head relative to the bone screw thereof, and the installation of a polyaxial cross connector head of the cross connector head assembly 100 onto the host spinal rod bone screw assembly head. The cross connector head assembly 100 utilizes a dual breakaway configuration rather than a single breakaway configuration as does the cross connector head assembly of FIGS. 1-9.

The cross connector head assembly 100 has a first portion 102, a second portion 106 and a driver portion 104. The first portion 102 provides a combination breakaway cross connector head 103 and set screw 154 for a spinal rod bone screw assembly (i.e. for a bone screw spinal rod head). The second portion provides an inner set screw and pivot 160 for the cross connector head 103 and an integral, breakaway inner set screw driver 163. The driver portion 104 provides a driver head 105 with a driver body 110 to install the first and second portions 102, 106.

The lower or set screw portion or collar 154 of the first portion 102 is generally cylindrical and includes external threads 156. In particular, these threads 156 are configured to be received by inner threads 243, 245 of the first and second sides 242, 244 of the spinal rod bone screw head 230 (see, e.g., FIGS. 14, 16 and 18). This allows the set screw portion 154 to threadedly press or compress against the taper lock 246 in order to press against the head 238 of the bone screw 220 for locking the orientation of the head 230 relative to the bone screw 220 (see, e.g., FIGS. 14, 16 and 18) during installation thereof. The cross connector head 103 is connected to the set screw portion 154 at or by a breakaway junction or juncture 158. The breakaway junction/juncture (minimum cross section area) 158 breaks when a torque limit is reached. This torque limit is controlled, at least in part, by the cross section area and the strength of the material. This allows the cross connector head 103 to rotate and maneuver free of the set screw portion 154.

The cross connector head 103 is generally U-shaped and thus defines first and second sides 150, 152. The first and second sides 150, 152 define a slot 155 for receipt of a cross connector rod (see, e.g. cross connector rod 306 of FIGS. 17 and 18) and particularly, of a flat portion (e.g. 307 or 309) of the cross connector rod 206. Additionally, the first side 1150 has a threaded inner surface 151, while the second side 152 has a threaded inner surface 152. The threads 151, 153 are configured to receive threads of a set screw 310 (see FIGS. 17, 18). The cross connector head 103 includes an internal bore 157 (see FIG. 12) that is threaded to threadedly receive a threaded shank portion 162 of the inner set screw and inner set screw driver (second portion) 106. In this manner, the threaded shank 162 contacts and compresses or presses against the spinal rod 250 to fix same.

The inner set screw and pivot 160 has a pivot portion 107 that sits atop the lower threaded shank (set screw) 162. The pivot portion 107 is generally ball shaped with an annular taper 161 extending from the shank 162 to a breakaway junction/juncture (minimum cross section area) 166 that is axially below the inner set screw driver 163. The pivot portion 107 pivotally (rotatably and/or axially) retains the cross connector head 103 relative to the collar 156. The inner set screw driver 163 axially extends from the breakaway junction 166 and includes a bore 164 that extends through the driver 163 (i.e. extends from one side to the other side of the driver 163 or extends generally transverse to the longitudinal axis of the driver 163). The driver bore 164 is sized to receive a driver pin 165. The breakaway junction 166 breaks when a torque limit is reached. This torque limit is controlled, at least in part, by the cross section area and the strength of the material. This allows the inner set screw and pivot 160 to remain while the driver 163 is removed during installation.

Figure 11:
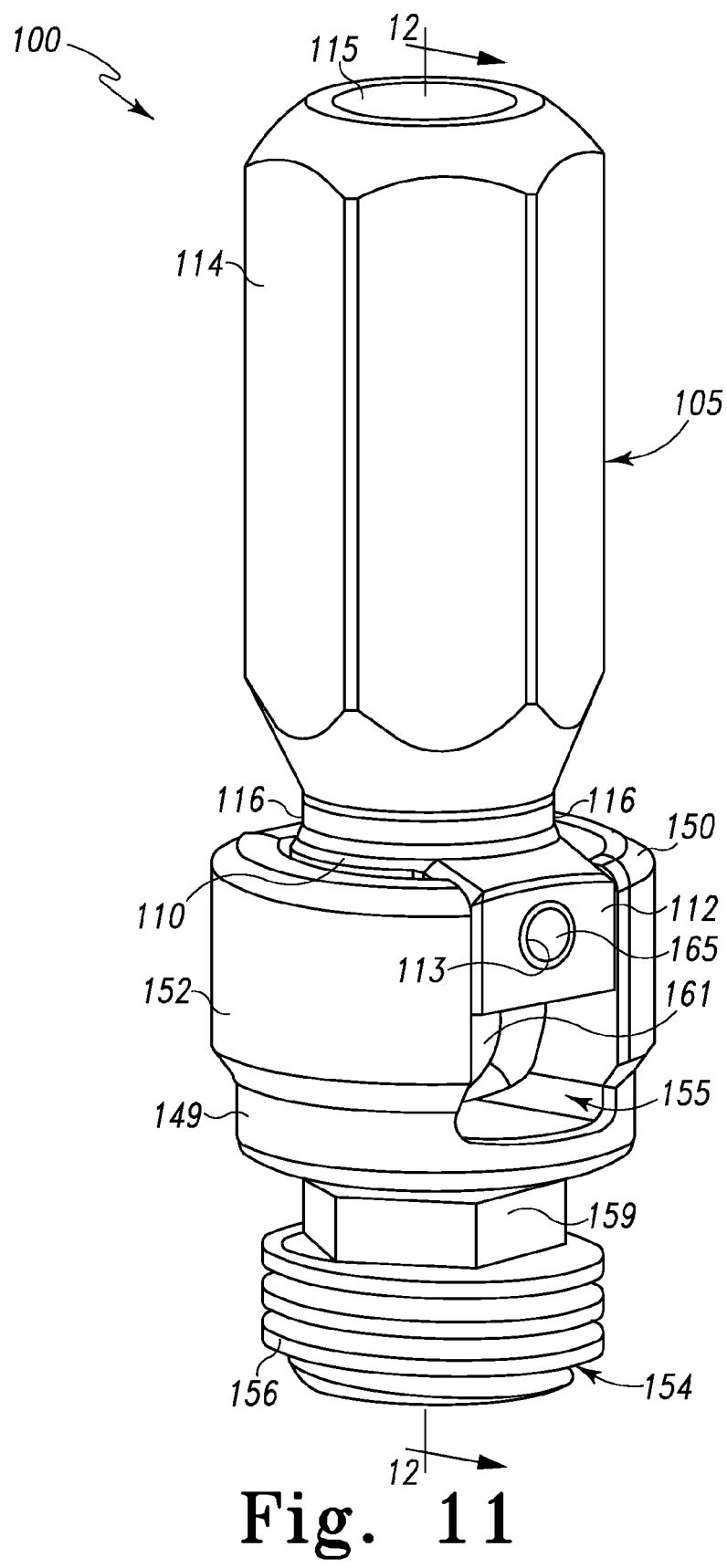
FIG. 11 is a perspective view of the cross connector head assembly of FIG. 10 shown in an assembled state before installation on a polyaxial spinal rod bone screw assembly.
Figure 12:
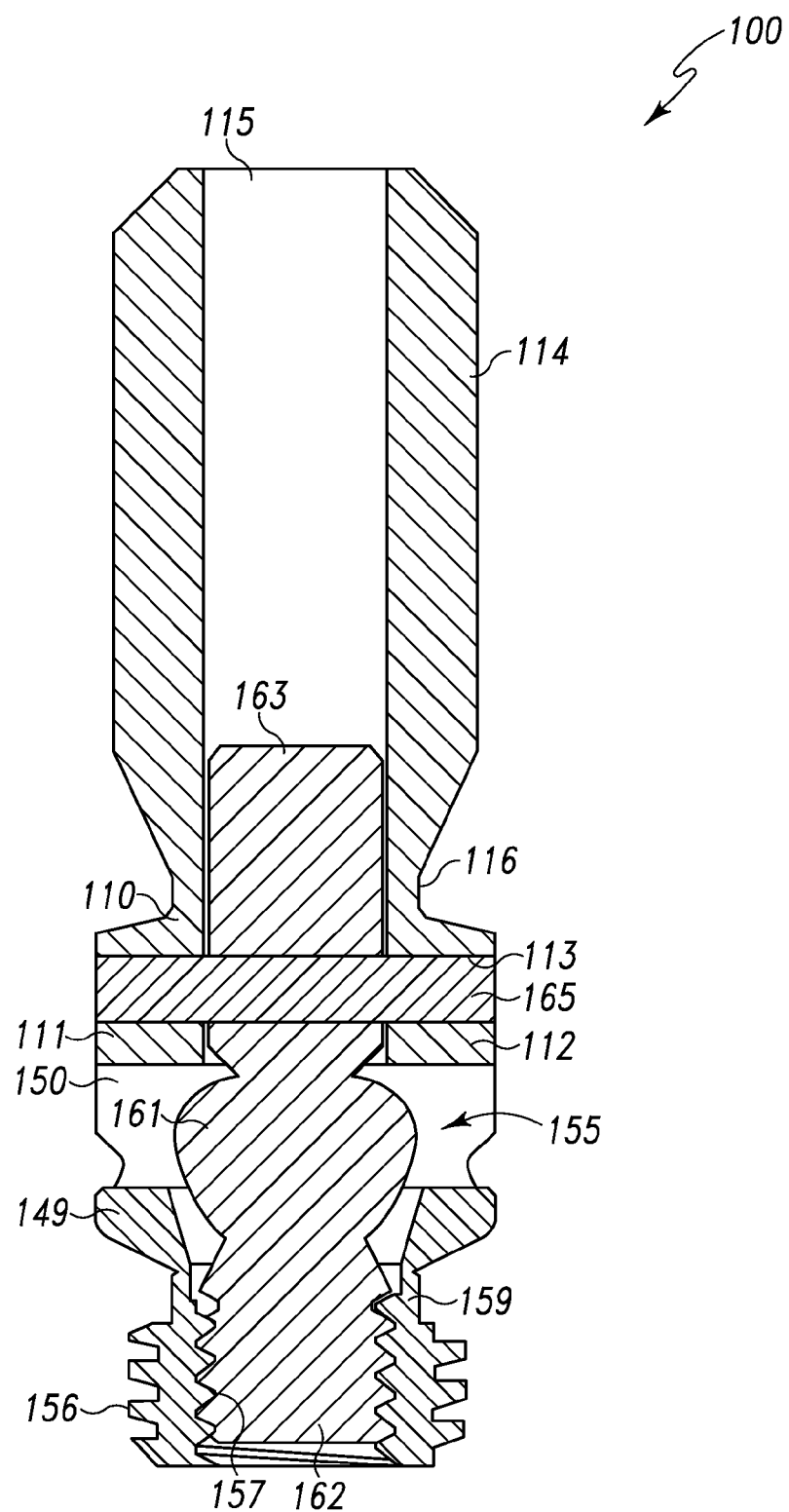
FIG. 12 is a sectional view of the cross connector head assembly of FIG. 11 taken along line 12-12 thereof.

The driver portion 104 is configured to install the cross connector assembly in conjunction with a driver tool (not shown) and, particularly, the first and second portions 102, 106 onto a spinal rod bone screw assembly. The driver portion 104 is characterized by an elongated body 105 having a hexagonal exterior 114 and an internal, axial bore 115, thereby forming a hexagonal driver/driver head. The hexagonal driver 105 is connected to a lower portion 110 via a reduced diameter portion 116. The lower portion 110 is sized to be received between the two sides 150 and 152 of the cross connector head 103. Moreover, the lower portion 110 includes a first flange 111 on one side thereof, and a second flange 112 on a second side thereof. The first and second flanges 111, 112 are sized to extend between the two open sides formed by the channel 155 (between the two sides 150, 152) such as can be seen in FIGS. 11 and 12. In this manner, rotation of the hexagonal driver 105 causes the flanges 111, 112 to abut the sides 150, 152 to rotate the cross connector head 103 (and the set screw 154). A driver bore 113 extends through the lower portion 110 from the first flange 111 to the second flange 112. This allows coupling of the driver portion 104 to the first and second portions 102, 106. As explained below, the driver portion 104 first installs the first portion 102 whereby when a first torque limit is reached the first portion 102 cleaves at the junction 158 to leave the collar 154 and allow the cross connector head 103 to rotate/angulate, then installs the second portion 106 whereby when a second torque limit is reached the second portion 106 cleaves at the junction 166 to leave the inner set screw and pivot 160 and allow the driver portion 104, the rod 165 and the driver 163 to be removed.

Figure 13:
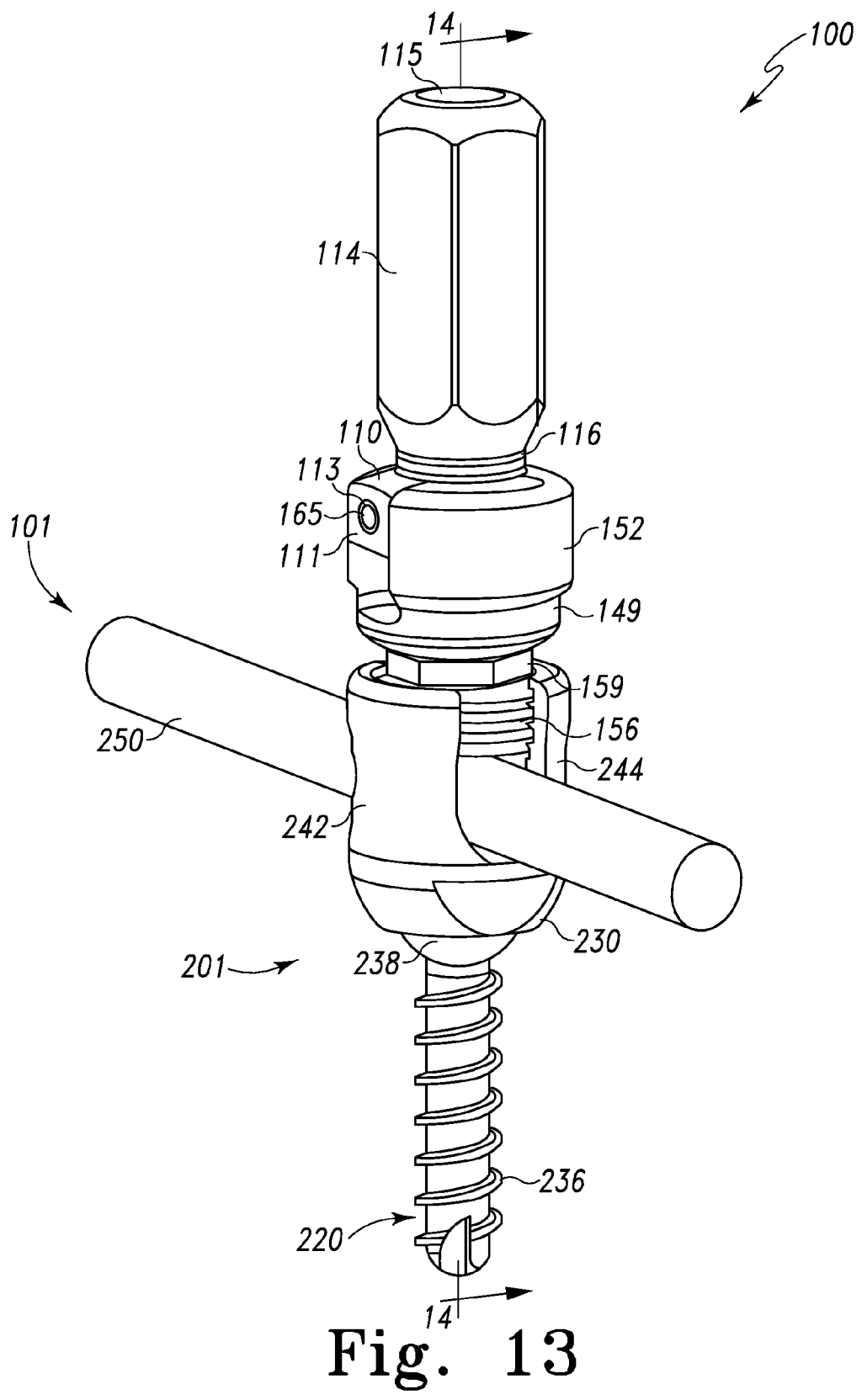
FIG. 13 is a perspective view of the cross connector head assembly of FIG. 10 shown assembled onto a polyaxial spinal rod bone screw assembly that holds a spine rod, the cross connector head assembly shown before final installation thereof onto the polyaxial spinal rod bone screw assembly.
Figure 14:
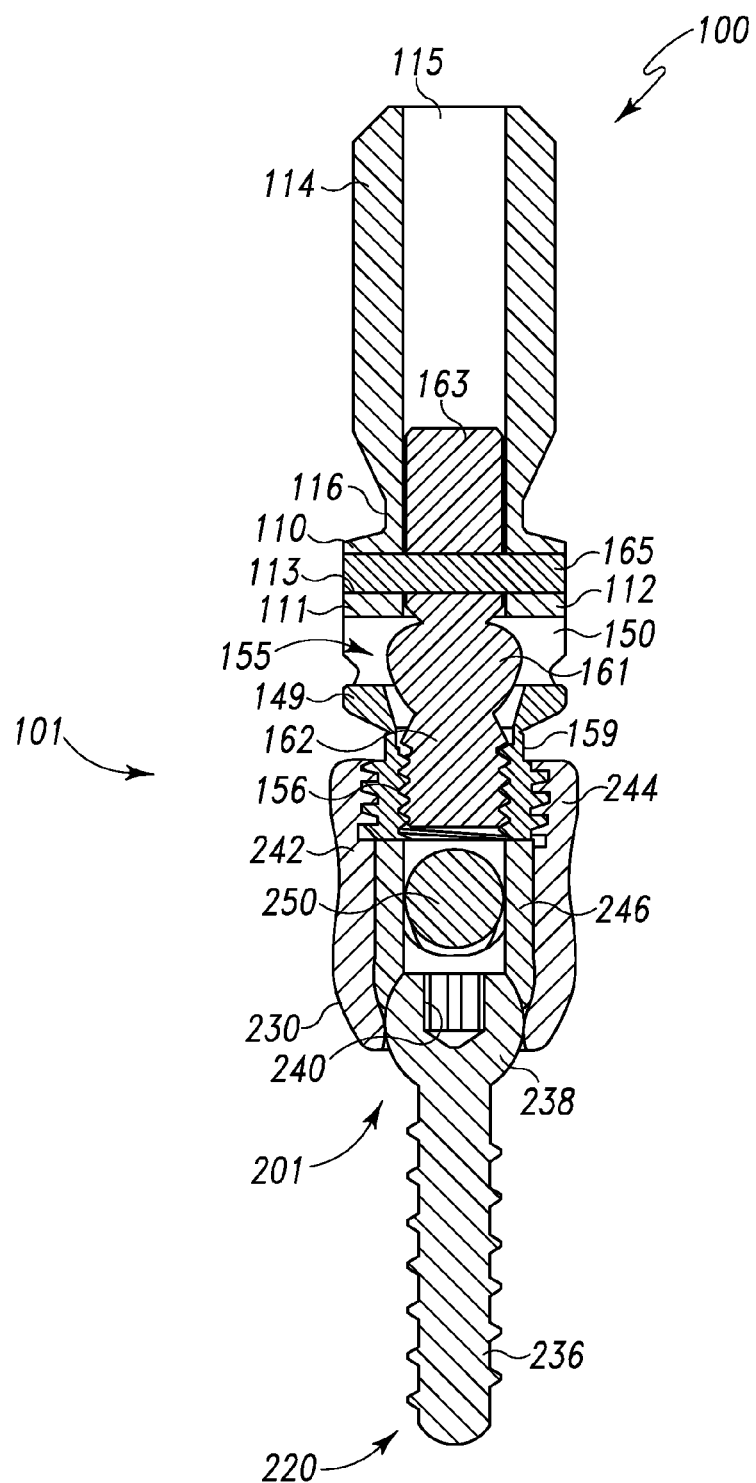
FIG. 14 is a sectional view of the cross connector head assembly of FIG. 13 taken along line 13-13 thereof.

FIGS. 13 and 14 depict a construct 101 defined as the cross connector head assembly 100 situated on a spinal rod bone screw assembly 201. The construct 101 depicts/is a pre-installation configuration whereby the cross connector head assembly 100 has been assembled and threaded onto the spinal rod bone screw assembly 201, the spinal rod bone screw assembly 201 being a polyaxial spinal rod bone screw assembly. The spinal rod bone screw assembly 201 is characterized by a bone screw 220 and a spinal rod head 230, the bone screw 220 having a threaded shank 236 that extends from a rounded head 238 which is pivotally retained by and extends from the spinal rod head 230. The spinal rod head 230 has side walls 242, 244 that each have internal threads 243, 245 for receiving the threaded collar 156.

Figure 15:
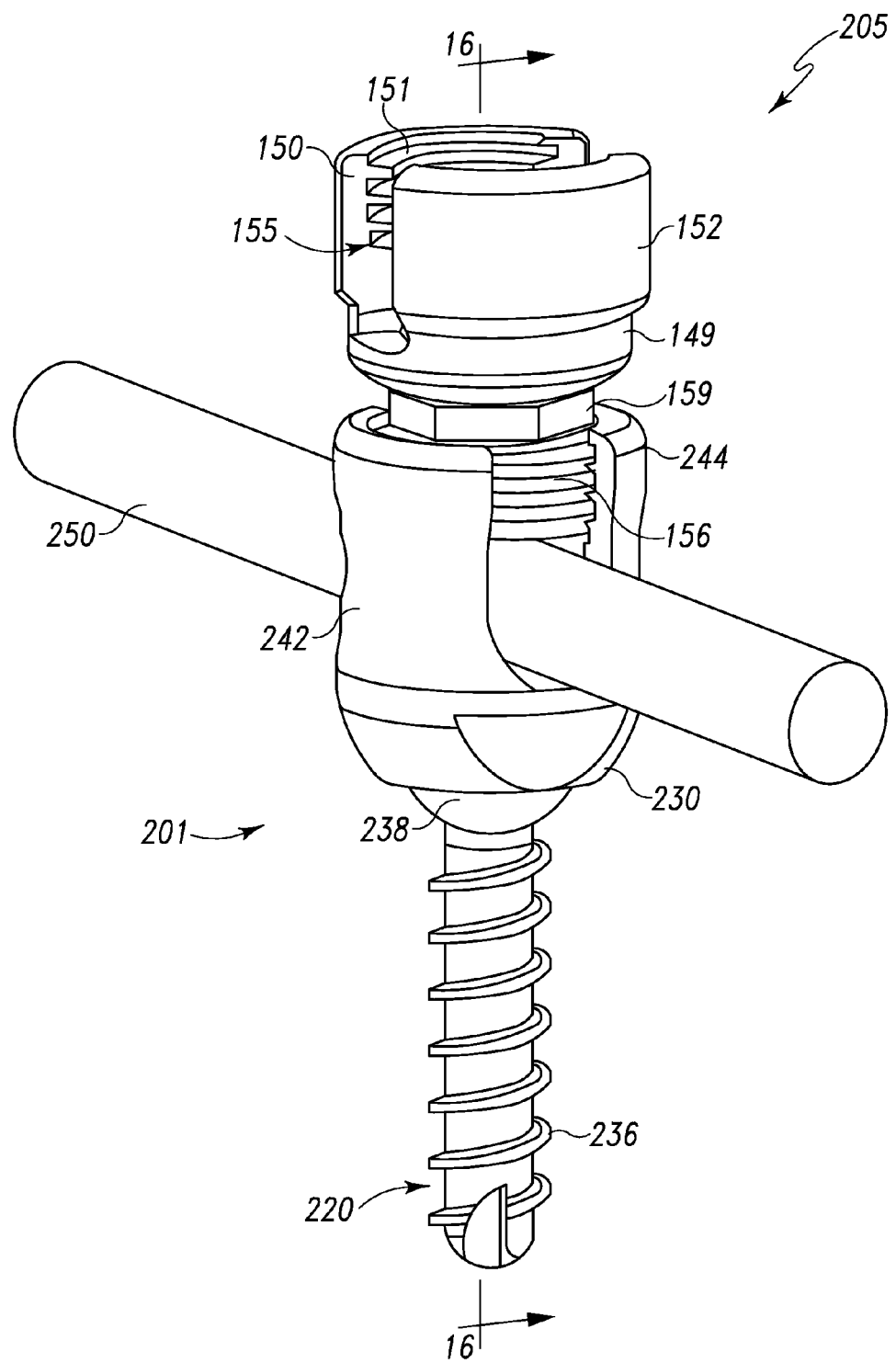
FIG. 15 is a perspective view of the cross connector head assembly mounted onto the polyaxial spinal rod bone screw assembly and spine rod of FIG. 13, the disposable components of the cross connector head assembly having been removed.
Figure 16:
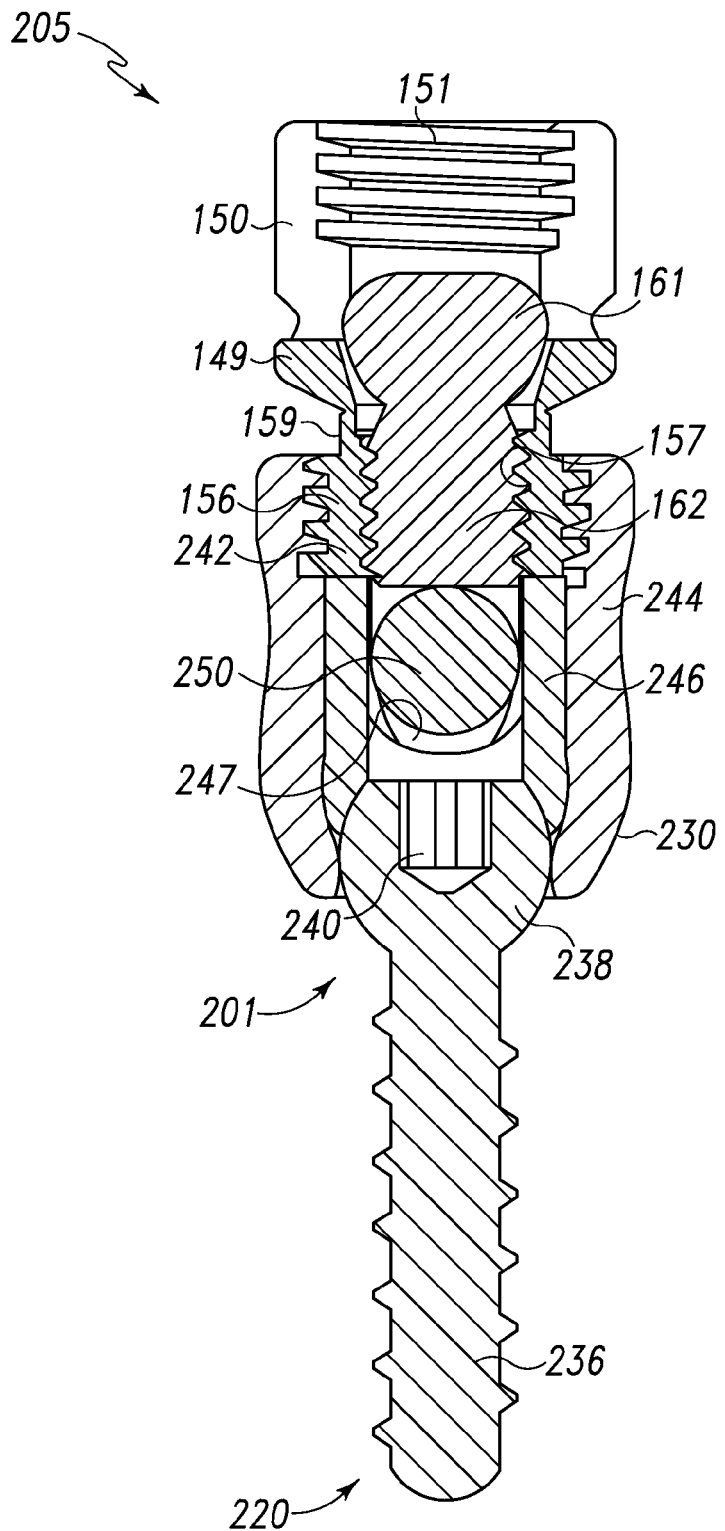
FIG. 16 is a sectional view of the cross connector head assembly and spine rod mounted onto the polyaxial spinal rod bone screw assembly of FIG. 15 taken along line 16-16 thereof.

As the hex driver 114 is rotated (threaded onto the polyaxial spinal rod screw head 230), the collar 246 interfaces with the taper lock 246 to fix the orientation of the head 230 relative to the screw 220. When a torque limit is reached, the cross connector head 103 breaks away or separates from the collar 156 such that the collar 156 is locked in place, while the cross connector head 103 is able to rotate freely about the ball 161. After the initial break, the assembly remains intact since the inner set screw 162 is pre-threaded in the center of the collar 156. The inner set screw 162 is now threaded downward into the center of the collar 156 via continued rotation of the driver 114. Since the pin or dowel 165 connects the driver 114 to the driver portion 163, continued rotation threads and sets the inner set screw 162 relative to the collar 156. After the inner set screw bottoms out on the spinal rod 250 and a torque limit is reached, the driver portion with its pin 165 and a portion of the ball 161 break off and are removed. FIGS. 15 and 16 depict what remains after the driver portion with its pin 165 and a portion of the ball 161 break off and are removed. A cross connector head is now ready to receive a cross connector rod (see, e.g. FIGS. 17 and 18) and have its orientation fixed.

Figure 17:
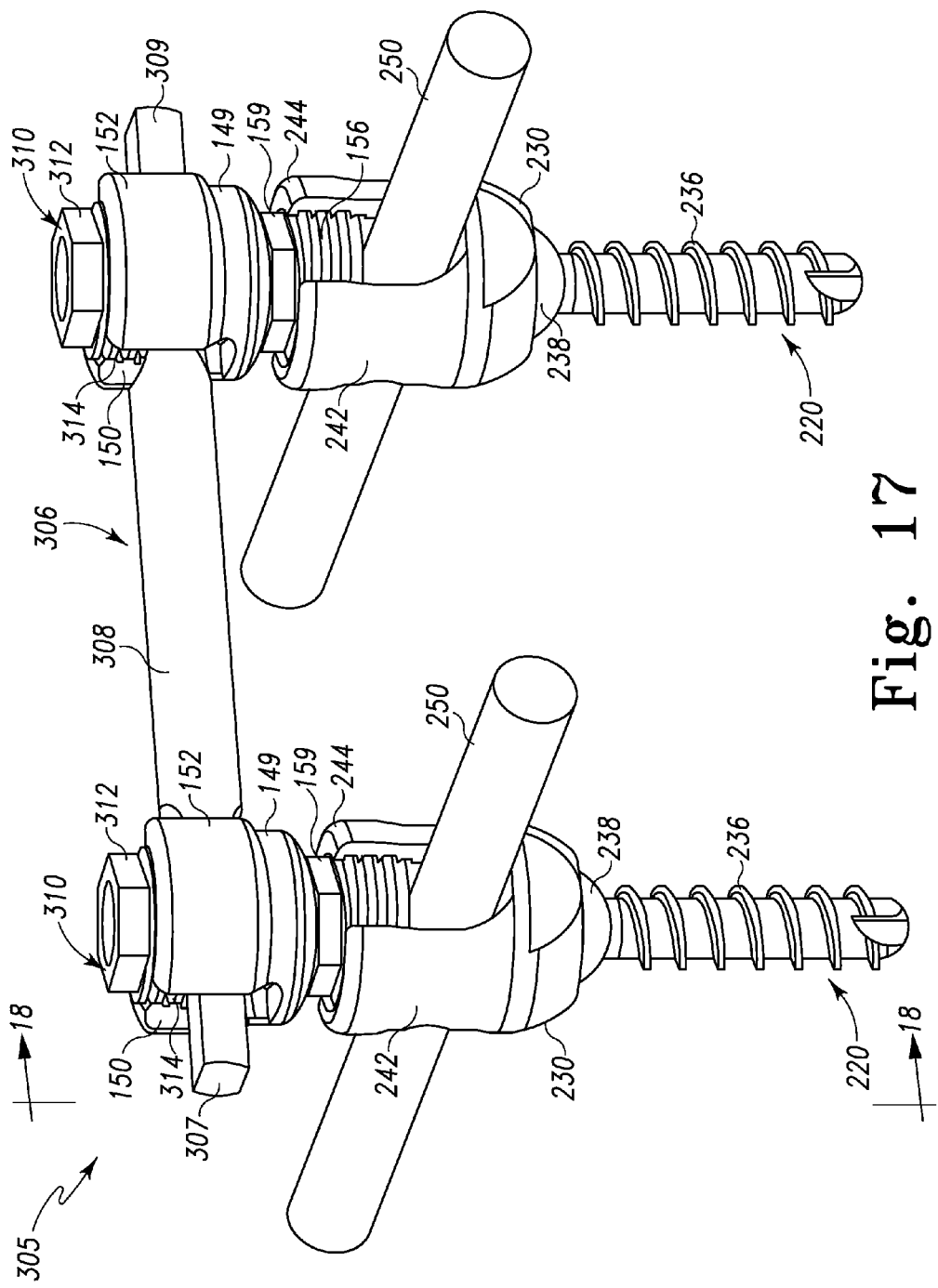
FIG. 17 is a perspective view of a spinal rod construct having a cross connector assembly mounted to adjacent spinal rod assemblies, the cross connector assembly using the cross connector head assemblies of FIGS. 10-16.
Figure 18:
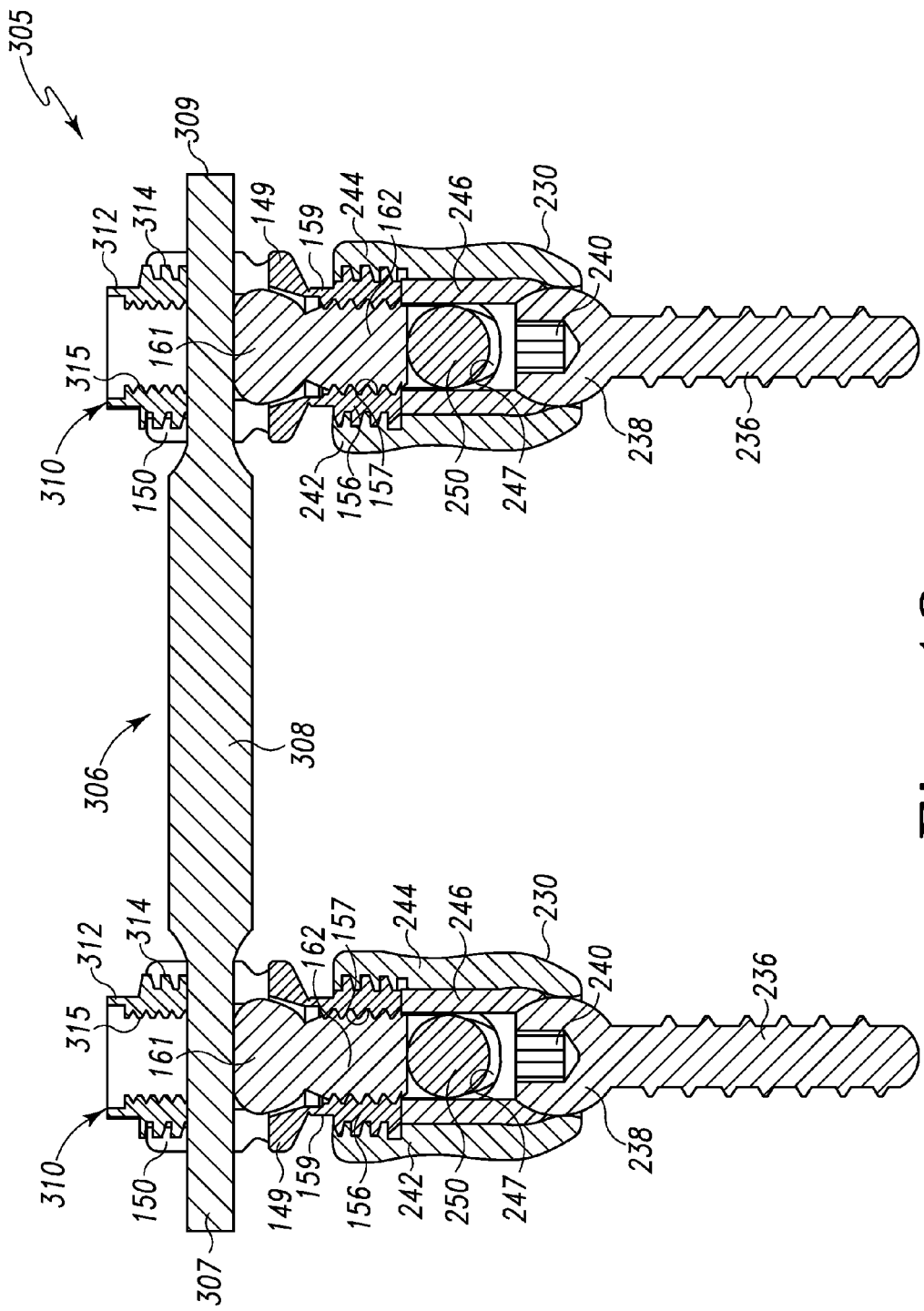
FIG. 18 is a sectional view of the spinal rod construct of FIG. 17 taken along line 18-18 thereof.

FIGS. 17 and 18 depict a cross connector construct 305 wherein a cross connector head assembly has been installed onto two spinal rod bone screw assemblies as described above. A cross connector rod 306 is connected to the cross connector heads such that a middle portion 208 extends therebetween. A first end 307 is captured in a first cross connector head, while a second end 309 is captured in a second cross connector head. A set screw 310 having a hex head 312 and externally threaded shank 314 is used to secure the respective ends of the cross connector rod into the cross connector heads.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should moreover be noted that the present invention is not necessarily exclusive to posterior cervical-thoracic screws, but is applicable to posterior thoracolumbar polyaxial screws as well.

What is claimed is:

1. A cross connector head assembly for use with a spinal rod bone screw assembly, the cross connector head assembly comprising:

a first portion configured as a combination collar for fixing an orientation of a spinal rod bone screw head to a bone screw of the spinal rod bone screw assembly and cross connector head for the spinal rod bone screw assembly, the cross connector head joined to the collar at a first minimum cross section area whereby application of a first torque limit separates the cross connector head from the collar;

a second portion configured as a combination set screw for fixing a spinal rod within the spinal rod bone screw assembly, retention pivot for pivotally retaining the cross connector head relative to the collar, and driver section for installing the second portion, the driver section joined to the retention pivot at a second minimum cross section area whereby application of a second torque limit separates the driver section from the retention pivot; and a driver portion configured for releasable coupling with the first and second portions and provide application of the first and second torque limits whereby the first and second portions are installed onto the spinal rod bone screw assembly.

2. The cross connector head assembly of claim 1, wherein the second portion is connected to the driver portion via a coupler.

3. The cross connector head assembly of claim 1, wherein the driver section of the second portion has a first bore extending generally transverse to a longitudinal axis of the second portion, the driver portion has a second bore extending generally transverse to a longitudinal axis of the driver portion, and a or coupler extends through the first and second bores.

4. The cross connector head assembly of claim 3, wherein the coupler comprises a dowel.

5. The cross connector head assembly of claim 3, wherein the driver portion includes first and second flanges configured for receipt in slots of the spinal rod bone screw head.

6. The cross connector head assembly of claim 5, wherein the second bore extends through the first and second flanges.

7. The cross connector head assembly of claim 1, wherein the driver portion has a hexagonal outer surface.

8. A spinal assembly for installing a spinal cross connector head onto a spinal rod bone screw assembly, the spinal assembly comprising:

a combination collar and cross connector head joined to the collar at a first minimum cross section area whereby application of a first torque limit separates the cross connector head from the collar, the collar configured to fix an orientation of a spinal rod bone screw head of the spinal rod bone screw assembly, and the cross connector head configured for attachment to the spinal rod bone screw head;

a combination set screw, retention pivot and driver section joined to the retention pivot at a second minimum cross section area whereby application of a second torque limit separates the driver section from the retention pivot, the set screw configured to fix a spinal rod within the spinal rod bone screw assembly, the retention pivot configured to pivotally retaining the cross connector head relative to the retention pivot for pivotally retaining the cross connector head relative to the collar, and the driver section configured to install the second portion; and a driver portion configured to releasably couple with the combination collar and cross connector head and the combination set screw, retention pivot and driver section, and to provide application of the first and second torque limits whereby the combination collar and cross connector head and the combination set screw, retention pivot and driver sections are installed onto the spinal rod bone screw assembly.

9. The spinal assembly of claim 8, wherein the combination collar and cross connector head is connected to the combination set screw, retention pivot and driver section driver portion via a coupler.

10. The cross connector of claim 8, wherein the driver section of the combination set screw, retention pivot and driver section has a first bore extending generally transverse to a longitudinal axis thereof, the driver portion has a second bore extending generally transverse to a longitudinal axis of the driver portion, and a coupler extends through the first and second bores.

11. The cross connector head assembly of claim 10, wherein the coupler comprises a dowel.

12. The cross connector head assembly of claim 10, wherein the driver portion includes first and second flanges configured for receipt in slots of the spinal rod bone screw head.

13. The cross connector head assembly of claim 12, wherein the second bore extends through the first and second flanges.

14. The cross connector head assembly of claim 8, wherein the driver portion has a hexagonal outer surface.

* * * * *